(12) United States Patent
Hoorn et al.

(10) Patent No.: US 6,703,408 B2
(45) Date of Patent: Mar. 9, 2004

(54) N-FORMYL DERIVATIVES OF PAROXETINE

(75) Inventors: Hans J. Hoorn, Nijmegen (NL); Theodorus H. A. Peters, Nijmegen (NL); Frantisek Picha, Brno (CZ)

(73) Assignee: Synthon BCT Technologies, LLC, Chapel Hill, NC (US)

( * ) Notice: Subject to any disclaimer, the term of this patent is extended or adjusted under 35 U.S.C. 154(b) by 0 days.

(21) Appl. No.: 10/274,051

(22) Filed: Oct. 21, 2002

(65) Prior Publication Data

US 2003/0125560 A1 Jul. 3, 2003

Related U.S. Application Data

(60) Provisional application No. 60/330,430, filed on Oct. 22, 2001.

(51) Int. Cl.[7] ............... A61K 31/445; C07D 405/12
(52) U.S. Cl. ........................... 514/321; 546/197
(58) Field of Search ............... 514/321; 546/197

(56) References Cited

U.S. PATENT DOCUMENTS

| | | | |
|---|---|---|---|
| 4,007,196 A | 2/1977 | Christensen et al. | 546/197 |
| 4,721,723 A | 1/1988 | Barnes et al. | 546/197 |
| 6,239,126 B1 * | 5/2001 | Kelly et al. | 514/211 |

FOREIGN PATENT DOCUMENTS

| | | | |
|---|---|---|---|
| EP | 0223403 B1 | | 8/1993 |
| EP | 0812829 A1 | | 6/1996 |
| EP | 802185 B1 | | 4/1997 |
| EP | 1074550 B1 | | 7/2000 |
| WO | WO 95/46448 | * | 6/1995 |
| WO | WO9853824 | | 12/1998 |
| WO | WO 99/58113 | * | 11/1999 |
| WO | WO0026187 | | 5/2000 |
| WO | WO0104093 A3 | | 1/2001 |
| WO | WO0104093 A2 | | 1/2001 |
| WO | WO 02/17921 | * | 3/2002 |

OTHER PUBLICATIONS

Fox et al. "Physics and chemistry of the organic solid state" Intersci. Pubs. p. 179–182 (1963).*

* cited by examiner

*Primary Examiner*—Ceila Chang
(74) *Attorney, Agent, or Firm*—Mark R. Buscher

(57) ABSTRACT

A compound or composition comprising N-formyl paroxetine of formula (1) is useful as a pharmaceutical and as a synthetic intermediate. The N-formyl paroxetine can be an impurity in paroxetine substances and methods of assaying for such an impurity are also useful.

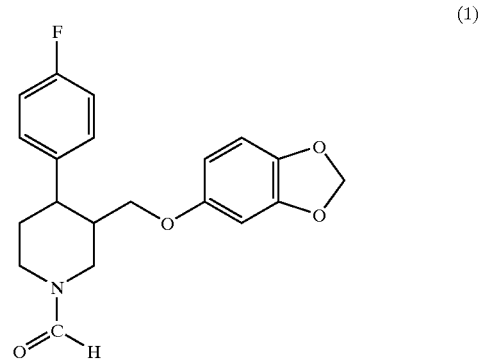

15 Claims, No Drawings

N-FORMYL DERIVATIVES OF PAROXETINE

This application claims the benefit of priority under 35 U.S.C. §119(e) from Provisional Application No. 60/330,430, filed Oct. 22, 2001, the entire contents of which are incorporated herein be reference.

BACKGROUND OF THE INVENTION

The present invention relates to N-formyl paroxetine compounds, to compositions containing the same and to uses thereof as an intermediate, as a reference marker or standard, and/or as a pharmaceutical active ingredient.

U.S. Pat. No. 4,007,196 describes 4-phenyl-piperidine derivatives including a compound that is now known as paroxetine. Paroxetine is a selective serotonin re-uptake inhibitor used to treat, inter alia, depression, obsessive-compulsive disorder, and panic disorder and has the following formula:

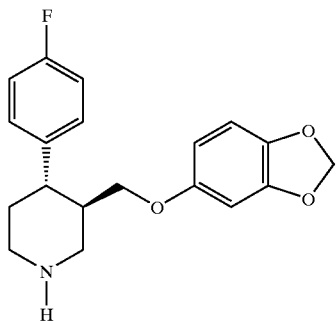

U.S. Pat. No. 4,721,723 and EP 223403 describe crystalline paroxetine hydrochloride hemihydrate. This particular form of paroxetine is the active ingredient in a commercial pharmaceutical tablet sold/made by SmithKline Beecham under such brand names as PAXIL® and SEROXAT™.

Pharmaceutical products are regulated in most countries by a government agency. For example, the U.S. Food & Drug Administration (FDA) generally requires an applicant to show safety and efficacy of the pharmaceutical product during the approval/review phase and requires monitoring of the safety of the drug post-approval. Similar requirements exist in many European countries and elsewhere in the world. In order to satisfy safety concerns, the regulatory agencies generally require a manufacturing specification that sets the maximum amount of each identified impurity as well as the maximum amount for all remaining unidentified impurities. Once approved, each batch or lot of the pharmaceutical product is tested to insure that the specification is met. Further, stability testing is performed on the pharmaceutical product in order to show that the composition does not substantially or materially change over time; i.e. over its indicated shelf-life. Good practice warrants keeping a sample from each batch which has been released to the public so that the stability of the product can be monitored over time and any defect uncovered and corrective action can be taken as appropriate.

Accordingly, pharmaceuticals are tested for purity both during manufacture and subsequently during its shelf-life. Typically, the product is tested by comparing certain analytical results with those of a standard reference result. For impurity detection, this normally means assaying the pharmaceutical product and comparing the result to the result obtained for a substantially pure form of the suspected impurity in the same assay. Sources of potential impurities in a pharmaceutically active agent or formulation include:

residual amounts of synthetic precursors
side product arisen from the synthesis and elaboration of the active substance
residual solvents
degradation products appearing during storage including products resulted from interactions with excipients in formulations
isomers of the active agent
trace contaminants e.g. from equipment and environment.

In terms of synthesis, paroxetine is most commonly described as being produced from either a carbamate derivative of formula (B), wherein R can be inter alia a phenyl group, or a methylenephenyl derivative of formula (C). Specifically, in the last step, using conditions that often employ high temperatures or expensive catalysts, a hydrolysis of the carbamate derivative or hydrogenolysis of the methylenephenyl derivative is performed to produce paroxetine.

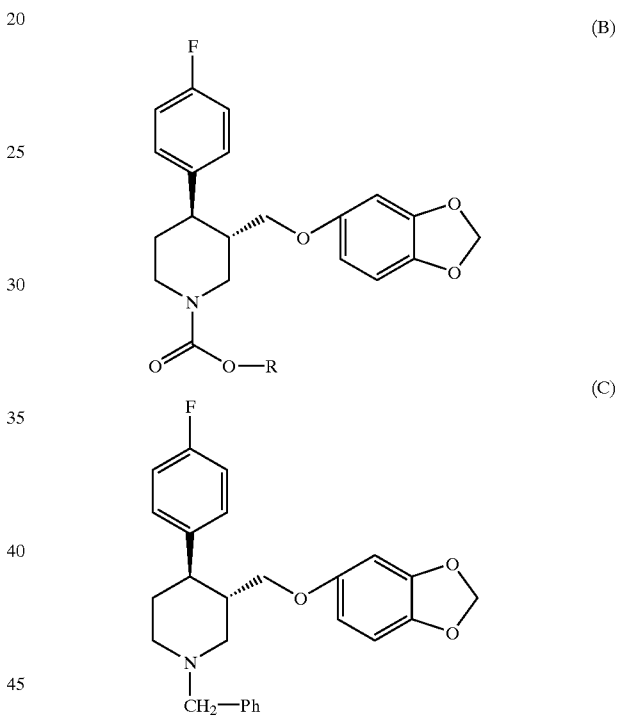

Thus, these compounds would be suspected as possible impurities in the paroxetine product produced according to these methods.

Several impurities for paroxetine hydrochloride were specifically identified in the published draft Monograph in Pharmeuropa Vol. 10, No. 2, June 1998, including desfluoroparoxetine, p-methoxyparoxetine, methylene bridged paroxetine dimmer, and N-methyl-4-(p-fluorophenyl)-tetrahydropyridine. This list is not exhaustive as other impurities, both identified therein and unidentified may exist within the tablet. Without identification of the potential impurity and a synthetic route to make a reference standard therefor, it is difficult or impossible to efficiently assay for a particular impurity or to otherwise monitor its level in the pharmaceutical product. Hence the need for a specification limit on the amount of unidentified impurities.

SUMMARY OF THE INVENTION

The present invention relates to the discovery/identification of a new compound, namely N-formyl paroxetine compounds, and to various uses thereof including the use of the compound in a new synthetic route for obtaining paroxetine and salts thereof. Accordingly, a first aspect of the present invention relates to a compound or composition comprising an N-formyl paroxetine of formula (1)

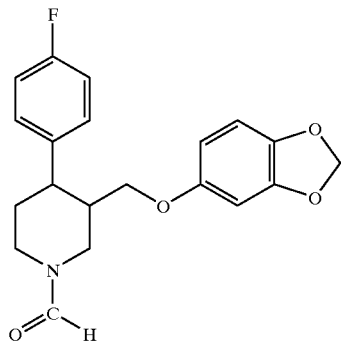

(1)

and 0 to 99.97% of a paroxetine compound, based on the combined weight of the N-formyl paroxetine and the paroxetine compound, if any. The N-formyl paroxetine compound can be an isolated, substantially pure single substance or part of a multi-component composition. The only limitation is that when a composition contains a paroxetine compound, then the amount of paroxetine is not greater than 99.97% based on the combined weight of both the paroxetine and the N-formyl paroxetine; i.e., at least 0.03% N-formyl paroxetine compound. Other than this proviso, the amount of N-formyl paroxetine is not limited. One specific compositional form relates to a pharmaceutical composition comprising an effective amount of the N-formyl paroxetine compound of formula (1) and optionally a paroxetine compound for treating a selective serotonin reuptake inhibitor-treatable disease or condition along with at least one pharmaceutically acceptable excipient.

A second aspect of the present invention relates to a process which comprises treating an N-formyl paroxetine compound of formula (1) with a de-formylation agent. The de-formylation agent can be acidic or basic and is preferably a pharmaceutically acceptable acid. In preferred embodiments, the treatment with the de-formylation agent directly produces a paroxetine salt such as a pharmaceutically acceptable salt. In some embodiments, this step completes a synthesis of paroxetine or a salt thereof. In these embodiments, the synthesis preferably uses a novel intermediate of formula (2) as is more fully described hereinafter.

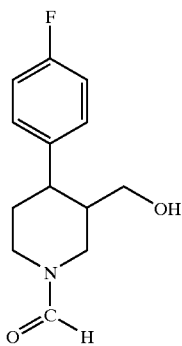

(2)

A third aspect of the present invention relates to a process for determining the stability or purity of a paroxetine substance or composition, which comprises assaying a paroxetine substance or composition for the presence of an N-formyl paroxetine of formula (1). The process can use TLC or HPLC and can be used for determining initial purity for product release or for stability testing.

In all aspects of the present invention, the N-formyl paroxetine compound is preferably the trans 3S, 4R enantiomer.

DETAILED DESCRIPTION OF THE INVENTION

The present invention is based on the discovery and identification of an impurity that can be associated with paroxetine, especially paroxetine pharmaceutical compositions as well as to the discovery of various uses thereof including as an intermediate in the synthesis of a paroxetine compound. In particular, an N-formyl paroxetine compound of formula (1)

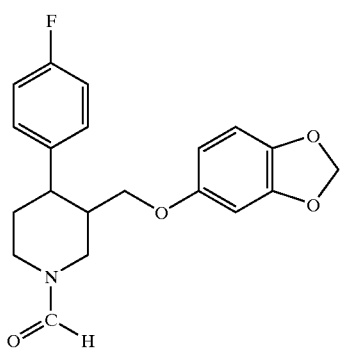

(1)

was isolated and identified as an impurity in a paroxetine mesylate pharmaceutical composition. The same impurity has also been found by the present inventors in commercially available paroxetine hydrochloride tablets from various European countries, albeit in small amounts that never exceed 0.02%. This is surprising in that N-formyl paroxetine is not a known intermediate in the synthesis of paroxetine nor is it otherwise a suggested or known potential impurity associated with paroxetine. Further, in some cases, storage of the paroxetine composition under accelerated conditions causes an increase in the amount of the N-formyl paroxetine compound.

Without wishing to be bound, it is theorized that the N-formyl paroxetine compound of formula (1) is formed by an interaction of paroxetine with excipients, particularly with calcium phosphate. In a model experiment, 5 g of paroxetine free base was mixed with 6.2 g $CaHPO_4$ and stored at approx. 80° C. for several days. The mixture was then stirred with 50 ml ethyl acetate and filtered. The filtrate was evaporated and the residue dissolved in 40 ml dichloromethane and filtered. The resulting product showed the presence of an "unknown" compound having the same retention time on HPLC chromatogram as the present N-formyl paroxetine compound of formula (1).

N-formyl paroxetine can be more fully named as 3-((1, 3-benzodioxol-5-yloxy)methyl)-4-(4-fluorophenyl)-1-piperidine carbaldehyde. Due to the two asymmetric carbons in the molecule, there may exist four single optical isomers and three racemic forms within the above formula (1). Preferably, the compound of formula (1) is essentially a single optical isomer or is essentially enriched by a single optical isomer, more preferably the single optical isomer (enantiomer) is the trans-3R, 4S configuration as shown in the following formula (1a):

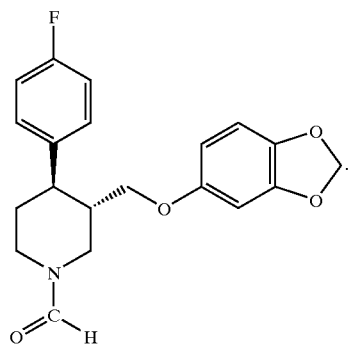

Dependant on the conditions of its production, isolation and/or purification, the compound of formula (1) may comprise various amounts of bound water or solvent. Thus, the N-formyl paroxetine of formula (1) may exist as a hydrate or a solvate in any of the compounds or compositions of the present invention. Preferably, the N-formyl paroxetine is an anhydrate, and as noted above, in the trans-3R, 4S configuration.

A compound or composition containing N-formyl paroxetine of the present invention is not particularly limited and embraces, inter alia, the substantially pure and isolated compound of formula (1), a mixture consisting of N-formyl paroxetine and a paroxetine compound, as well as a composition containing N-formyl paroxetine in minor amounts. The only limitation is that if a paroxetine compound is present in the compound or composition, e.g., as an impurity, as a co-active agent, etc., its relative amount is limited to being not greater than 99.97%, based on the combined weight of N-formyl paroxetine and the paroxetine compound. As used herein, the term "paroxetine compound" means paroxetine as a free base as well as any salt thereof including but not limited to pharmaceutically acceptable salts thereof. The compound or composition can be in any state of matter including a solid form such as a crystalline or amorphous material, a powder blend or a mixture, or in a liquid form such as an oil or in a dissolved state.

In certain embodiments no or very little paroxetine compound is present, such as from 0 to 5%. This includes the paroxetine compound being essentially absent from the compound or composition, i.e. below detection limits on HPLC or similar apparatus to trace amounts such as 0 to 0.01%. These embodiments include compositions that additionally contain other, non-paroxetine compounds, especially pharmaceutically acceptable excipients as in a pharmaceutical composition discussed hereinafter. Alternatively, the compound or composition containing N-formyl paroxetine can also be substantially free of all other compounds. In this embodiment, the N-formyl paroxetine compound is substantially pure and isolated. Typically such a pure and isolated form contains no more than 10% total impurities, i.e., substances other than the N-formyl paroxetine compound of formula (1), more preferably not more than 5% total impurities, more preferably not more than 1% total impurities. In its isolated state, the compound (1) is typically an oil, but any liquid, semisolid modification of the compound, or solid form is also considered within the present invention.

In some preferred embodiments, the N-formyl paroxetine compound of formula (1) is combined in a composition with a paroxetine compound, wherein the amount of paroxetine compound is within the range of 0.1 to 99.95%, preferably 1.0 to 99.89%, more preferably 1.0 to 99.98%, and more preferably 10 to 99.7%. The paroxetine compound is preferably selected from the group consisting of paroxetine, paroxetine hydrochloride, paroxetine maleate, paroxetine acetate, and paroxetine mesylate, although any other salt of paroxetine may be used as mentioned above. Further, the composition can contain additional components such as a pharmaceutically acceptable excipient. Suitable excipients are well known in the art and include binders, fillers, carriers, lubricants, release modifying agents, colorants, flavoring agents, solubilizing agents, disintegrants, and preservatives. A calcium phosphate is a preferred class of excipient and includes all calcium and phosphate-containing materials including calcium phosphate, calcium hydrogen phosphate anhydrate, calcium hydrogen phosphate dihydrate, etc., as is well known in the art.

Preferred forms of each of the above-described compositions include pharmaceutical compositions for treating a selective serotonin reuptake inhibitor-treatable disease or condition, comprising an effective amount of a paroxetine agent and at least one pharmaceutically acceptable excipient, wherein the paroxetine agent consists of an N-formyl paroxetine compound of formula (1) and optionally a paroxetine compound. It is believed that N-formyl paroxetine is converted to paroxetine or paroxetine hydrochloride salt in vivo due to the acidic nature of the stomach. Thus, N-formyl paroxetine either alone (0% paroxetine compound) or in combination with a paroxetine compound (up to 99.97% paroxetine compound) can be used as the active agent. The proportion of N-formyl paroxetine compound to paroxetine compound can be in accordance with any of the above-described ranges; i.e., 0 to 5% paroxetine compound; 0.1 to 99.95% paroxetine compound; etc., and is more typically a 0:100, 10:90, 20:80, 30:70, 50:50, 70:30, 80:20, 90:10, 95:5, or 99:1 weight ratio of paroxetine compound to N-formyl paroxetine compound of formula (1). Again the paroxetine compound is preferably selected from the group consisting of paroxetine, paroxetine hydrochloride, paroxetine maleate, paroxetine acetate, and paroxetine mesylate, although other pharmaceutically acceptable salts may also be used. Serotonin re-uptake inhibitor-treatable diseases or conditions include any disease or condition that would benefit from inhibition of serotonin re-uptake and includes, but is not limited to, depressions, anxiety, obsessive-compulsive disorder, obesity, alcoholism, and social phobia. Excipients include any inert or non-active material used in making a pharmaceutical dosage form as described above. For example, tablets may include, but are not limited to, a calcium phosphate, a cellulose, a starch and/or lactose. Capsules such as those made of gelatin, may contain or carry the active agent alone or in admixture with other excipients. Liquid dosage forms are also included such as oral liquids in the form of liquors or suspensions.

The pharmaceutical composition is normally provided in a unit dose. A unit dose may be typically administered once or twice daily, more typically once daily. An effective amount of the paroxetine active agent in a unit dose is generally within the range of 1 to 100 mg, typically 1 to 50 mg, more typically 1 to 20 mg, including 5, 10, 20, 30, and 40 mg doses.

All of the pharmaceutical compositions can be made by known methods and techniques. For example, the tablets can be made by dry granulation/direct compression or by a classical wet granulation method. Typically, tablets are made by blending, filling and compressing into tablets. The blending step may comprise a wet granulation or dry granulation. Similarly, capsules can be made by blending the ingredients and filling the capsule.

The N-formyl paroxetine compound of formula (1) of the present invention may be prepared by various processes. For instance, it may be produced by coupling the compound of formula (2) with a compound of the formula (3).

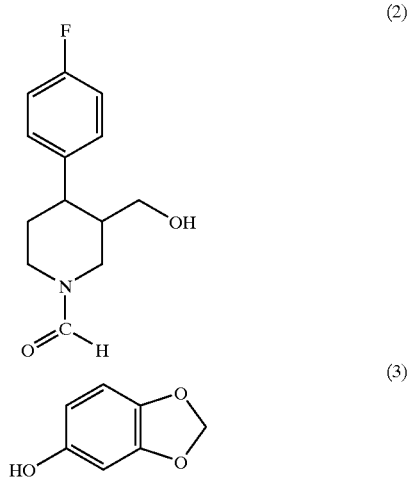

"Coupling" can be achieved in a variety of ways such as by using dicyclohexyl-carbodiimide (DCC) as a coupling reagent or using conditions of so-called Mitsunobu reaction (see WO 01-04093 for details). Optionally, the coupling can involve first converting compound (2) to a reactive derivative thereof especially the ester of an alkyl- or aryl-sulfonic acid and then reacting it with the compound of formula (3) to form N-formyl paroxetine compound of formula (1).

The starting compound of formula (3) is known as sesamol and is commercially available. The starting compound of formula (2) is novel per se but can be prepared by formylation of a compound of formula (4)

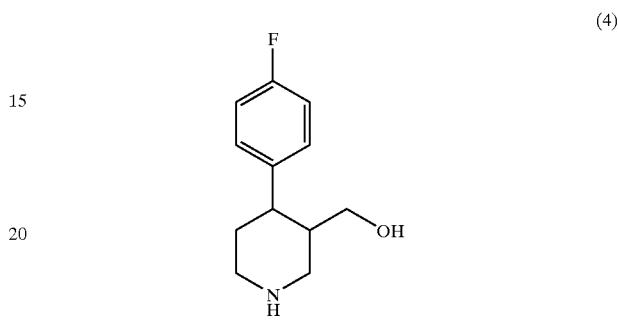

which in turn is preparable by various methods described in EP 802185, EP 812829, WO98-53824, EP 1074550 or WO00-26187.

The synthetic routes are exemplified in the following scheme:

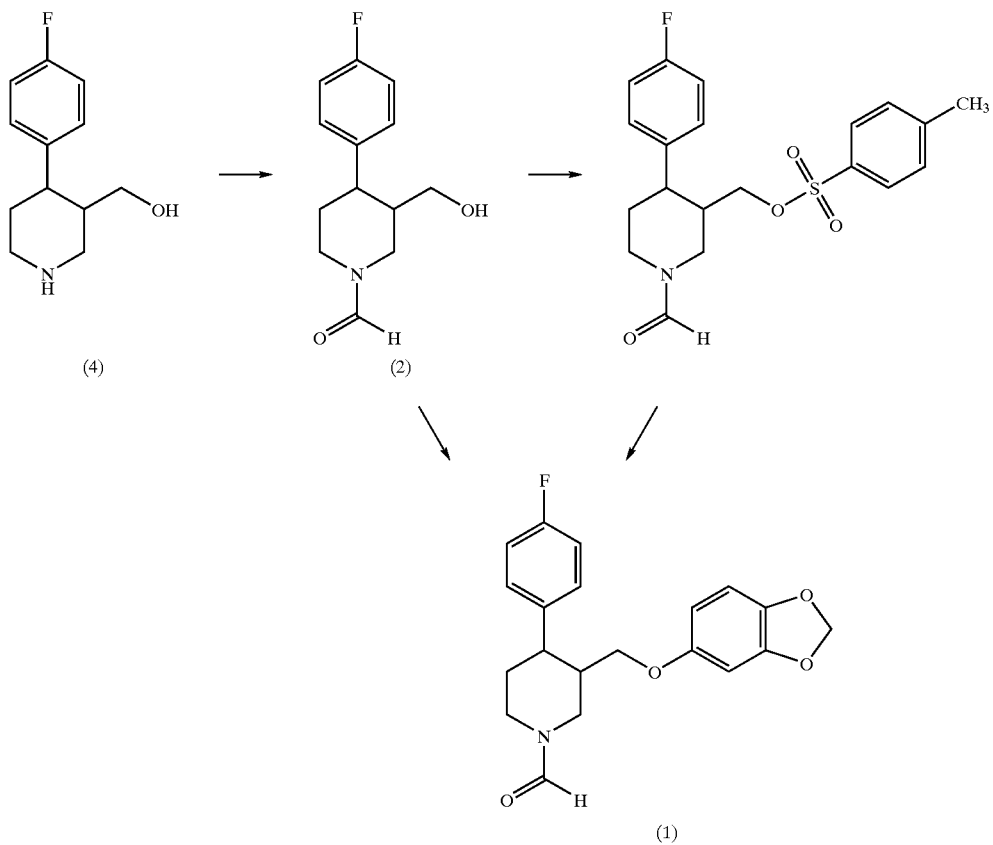

where a tosylate ester is used to illustrate the optional route of first forming an active ester derivative before reacting with a sesamol compound. It should be understood that the optional route is not so limited.

Useful formylation agents for conversion of the compound (4) to compound (2) include formic acid or a formic acid/acetic anhydride mixture, but are not limited thereto. The reaction can be carried out in a solvent but typically the formylation agent is used as the solvent as well. The reaction temperature is typically from ambient to the boiling point of the solvent or reactants, optionally under superatmospheric or reduced pressure.

The desired enantiomer of N-formyl paroxetine, especially the trans-3R, 4S enantiomer can be made by starting with the 3R, 4S compound of formula (4). Alternatively, the isomeric blend can be purified by known methods and techniques including the use of stereo-specific salts and fractional crystallization.

Alternately, the compound (1) can be prepared by formylation of paroxetine with a formylation agent. Typically the reaction involves treating paroxetine free base with formic acid/acetic anhydride mixture, optionally under enhanced temperature, whereby the mixture serves also as a solvent for the reaction. The course of the reaction may be advantageously monitored by a suitable chromatographic method, e.g. by HPLC. After removal of the excess of the formylating agent, the compound (1) may be isolated from the reaction mixture by conventional methods or it may be even used in crude state as a degree of conversion higher than 95% may be easily obtained.

This method of production of compound (1) is especially advantageous when the compound of formula (1) is to be prepared and industrially used in a small scale, e.g. for use as a reference marker where only milligram amounts are required. The advantage is based on the fact that paroxetine is readily available and the conversion process comprises only one reaction step.

The N-formyl paroxetine compound of formula (1), regardless of how it was made, can be used to form a paroxetine compound. Specifically, the N-formyl paroxetine compound of formula (1) is treated with a de-formylation agent. In general terms this treatment results in a type of solvolysis, usually a hydrolysis reaction, whereby the formyl group is removed. The "treating" step can be accomplished in a solid state, in a suspension, in a two phase state or in a liquid or solvent. The suitable treatment conditions preferably comprise dissolving or suspending the compound (1) in a suitable protic solvent, e.g. in water, a lower alcohol and mixtures thereof, and adding sufficient amount of a de-formylation agent, usually at least one molar equivalent and preferably a slight molar excess. A suitable lower alcohol is methanol or ethanol. Advantageously, the de-formylation agent is also dissolved in a suitable solvent. The temperature of the reaction is preferably from 0° C. to a boiling point of the solvent, most preferably about 50° C. The de-formylation agent may be added at once, in portions, or continuously. The protic solvent may also be used in a mixture with an aprotic solvent.

The de-formylation agent is not particularly limited and includes acidic and basic reagents. Acidic de-formylation agents include organic and inorganic acids. Typically the acidic formylation agent is a pharmaceutically acceptable acid, such as hydrochloric acid, acetic acid, formic acid, methane sulfonic acid, maleic acid, and tartaric acid. Basic reagents are typically strong bases such as sodium hydroxide.

The product obtained from the treating of an N-formyl paroxetine compound of formula (1) with a de-formylation agent depends in part on the nature of the reagent and the reaction, i.e., hydrolysis or solvolysis. In general, a basic de-formylation agent produces paroxetine free base, which can be isolated by conventional methods from the reaction mixture, in solid, oil, or dissolved state. In some embodiments the free base of paroxetine is preferably converted to an acid addition salt thereof, with or without prior isolation of the free base. The acids are preferably pharmaceutically acceptable acids as described above. Preferred acids include hydrochloric acid, acetic acid, sulfonic acids (methane sulfonic acid etc.) and maleic acid, although other acids that form pharmaceutically acceptable acid addition salts may be used. The methods of converting paroxetine into salts are well known in the art.

An acidic de-formylation agent generally converts the N-formyl paroxetine into a corresponding acid salt of paroxetine. The paroxetine salt can be in dissolved form or in precipitated form as a solid, or both forms, as a result of the treating step depending on whether a solvent is used, the nature of the solvents and the relative solubilities of the paroxetine salt, the concentrations of reagents, etc. Thus, a treating step that uses acidic de-formylation agents in carrying out a hydrolysis reaction is especially advantageous in the case where the desired paroxetine compound is a paroxetine salt as it can be formed in one step from the N-formyl paroxetine compound of formula (1) without the need to isolate or otherwise deal with a paroxetine free base intermediate.

Two particularly preferred embodiments involved the use of methane sulfonic acid and hydrochloric acid as the de-formylation agent. The hydrolysis of the compound (1) in the presence of methane sulfonic acid requires generally milder reaction conditions than in the use of a basic de-formylation agent such as sodium hydroxide. Further, the result of the treating step is the formation of paroxetine methane sulfonate in a dissolved form (i.e., protonated paroxetine free base dissociated from acid moiety anion), liquid/oil form or in a solid/precipitated form. The paroxetine methane sulfonate is preferably in crystal form either as a spontaneous result of the treating step and associated conditions or by the use of crystallization techniques including dissolving the isolated product in a different solvent, the use of a seeding crystal, changing the temperature and/or changing the volume of solvent.

Treating with a hydrochloric acid de-formylation agent results in the formation of paroxetine hydrochloride. This includes the various solid forms of paroxetine hydrochloride such a crystalline paroxetine hydrochloride hemihydrate, crystalline paroxetine hydrochloride anhydrates, amorphous paroxetine hydrochloride, etc. Also included are the dissolved forms. In one preferred embodiment, the treating step occurs in vivo. Specifically, an N-formyl paroxetine compound of formula (1) may act as a pro-drug of paroxetine, i.e. it may be metabolized in such a way that paroxetine is formed in the human or animal body by a biochemical conversion comprising essentially the hydrolysis of the formyl group of compound (1). Thus, the treating step embraces the contacting of ingested N-formyl paroxetine of formula (1), possibly as part of a pharmaceutical composition, with the de-formylation agent of hydrochloric acid in the stomach. The result of the treatment is paroxetine hydrochloride as a dissolved salt or as a solid precipitate in any of the forms described above.

The course of the hydrolysis reaction may be monitored e.g. by measuring and evaluating the amount of residual compound (1) in the reaction mixture by any suitable method, e.g. by HPLC or TLC, advantageously using the principles and techniques described above for the use of compound (1) as a reference marker. The reaction is recommended to be stopped as soon as the amount of the compound (1) in the reaction mixture drops below a chosen limit, e.g. below 1% of the initial charge.

The N-formyl paroxetine compounds of formula (1) are also useful in determining the stability or purity of a paroxetine substance or composition as a reference standard or marker. Specifically, a paroxetine substance or composition (sometimes a "paroxetine material") can be assayed for the presence of, and optionally the amount of, the now identified impurity of N-formyl paroxetine of formula (1).

The paroxetine material to be assayed for the presence of compound (1) comprises paroxetine substances and compositions. The term "paroxetine substance" is used herein to denote a material that contains primarily only paroxetine free base and/or salt(s) thereof, optionally in a solvated or a hydrated state. The paroxetine per se can be of any suitable physical form including crystalline forms or amorphous forms. Examples of the substance include the reaction mixture comprising paroxetine, crude paroxetine recovered during synthesis as well as purified paroxetine. "Paroxetine compositions" include mixtures, blends, solutions, suspensions, etc. that contain paroxetine substance (as hereinabove defined). Examples of compositions include the blended, powdery composition used in tabletting techniques to form tablets as well as intermediates therefore and final dosage forms. The compositions may be further processed in order to carry out the assay, i.e. crushing a tablet to obtain a powder, and such modifications are included within the scope of the composition.

A preferred paroxetine composition to be tested is a paroxetine pharmaceutical composition, especially a solid dosage form thereof. A pharmaceutical solid dosage form includes tablets, capsules, sachets, etc. that comprise paroxetine, in a pharmaceutically effective amount, and at least one pharmaceutically acceptable excipient such as a binder, filler, diluent, lubricant, disintegrant, etc. Such compositions are made by methods well known in the art including wet granulation, dry granulation and direct compression for tablets and blending and filling for making capsules. In both cases, a blend is formed by blending paroxetine with at least one pharmaceutically acceptable excipient. The blend is then further processed including filling it into capsules or compressing it into tablets as desired. It should be noted that blending or granulating embraces both wet and dry processing methods. Examples of paroxetine compositions include a paroxetine hydrochloride tablet, tablet core, and tabletting composition. Because stability of a pharmaceutical composition is important, the paroxetine pharmaceutical composition to be assayed may have been stored for at least 3 months prior to carrying out the assay. The storage can be under elevated temperature and/or elevated humidity, so-called accelerated storage, or at room temperature and can last for three months, six months, nine months, twelve months, eighteen months or twenty four months.

The assaying technique useful in the present invention is not particularly limited and includes any technique that can resolve or otherwise detect the presence of N-formyl paroxetine. In general, assays can be divided into techniques based on physical separation of the target compound(s) from the sample and non-separating or observation-based techniques such as IR and NMR, although other techniques are also possible. Preferably the assay is based on a separation. Examples of this type of assay include thin layer chromatography (TLC) and high performance liquid chromatography (HPLC).

As the present invention allows for preparing an N-formyl paroxetine compound of formula (1) in a sufficiently pure state, this compound can be used as a reference standard (or reference marker) in a novel process (assay) for testing the purity and/or stability of a sample of paroxetine substance or paroxetine composition. As a reference standard, the compound (1) should be in a suitably pure form, typically at least 80%, more preferably at least 90%. Higher purity levels are attainable, but are not essential. The compound (1) produced as described above may be further purified if necessary to achieve the desired purity level. Purification may be carried out by conventional methods; for instance, by recrystallization from a suitable solvent, by preparative chromatography or by stirring, optionally under heating, a suspension of the compound in a suitable liquid with subsequent removal of the liquid phase.

The compound (1) is assayed under a set of conditions to produce a reference standard analytical result. A "reference standard analytical result" may be a quantitative or qualitative result and can be in any form including numerical, graphical, pictorial, etc. In some cases the result can be stored electronically for later comparisons. In practice, the assaying of the paroxetine substance or composition results in an analytical result for the sample. This "sample analytical result" is typically compared in some fashion to the reference standard analytical result for the N-formyl paroxetine compound of formula (1). The comparison can be done manually such as by visual observation and/or by an automated procedure. The reference standard analytical result can be obtained essentially concurrently with the sample analytical result such as immediately before, during or immediately after the assaying of the paroxetine sample, or it can be obtained earlier, even months or years earlier. In some embodiments the reference standard analytical result is electronically stored and used by a computer algorithm to determine the presence of the compound (1) and its amount. This latter embodiment includes calibrating the equipment based on the reference standard analytical results or results derived therefrom and/or providing a so-called internal normalization. All such comparisons, whether direct, indirect, manual or automated, are included within the meaning of "comparing."

The invention also provides the use of the compound (1) as a reference marker in analyzing the purity or stability to degradation of a batch sample of paroxetine or a batch sample of a pharmaceutical dosage form comprising paroxetine. Such analytical testing of the drug substance or the drug form comprising paroxetine serves principally to confirm that compound (1) is absent (i.e. below the detection limit of the analytical method) or is only present at a level below the maximum allowed limit characterizing the pharmaceutical quality of products comprising paroxetine. i.e. a quality allowing the products to be released or sold as pharmaceuticals.

The assay used in determining the reference standard analytical results is generally also the same assay with the same set of conditions used to test the paroxetine material, although such is not necessarily required.

The invention will be further described with reference to the two preferred assay techniques, namely TLC and HPLC. In TLC, samples of the tested paroxetine material, and reference standard of compound (1) are chromatographed on a suitable chromatographic plate by a suitable developing liquid (mobile phase) under set conditions. These conditions include the solvent, the concentration of the samples in the solvent and the amount of solution applied to the plate. Selecting appropriate solvents and concentrations is well known within the art. The analytical results produced under these conditions may include the Rf value, namely the ratio of distance traveled by the corresponding material to the distance traveled by the solvent, and/or the size of the spot produced on the chromatogram.

Preferably, the reference standard is applied at the same time and to the same chromatographic plate as the tested sample thereby allowing for side-by-side comparisons. In other embodiments the reference standard is already defined and is simply compared with the developed sample chromatogram.

Thus one process for testing the purity and/or stability to degradation of a sample comprising paroxetine comprises the steps of:

a) dissolving a sample comprising paroxetine in a solvent to produce a sample solution b) dissolving a sample of compound (1) in a solvent to produce a reference 20 solution c) subjecting the sample solution and the reference solution to thin layer chromatography to obtain a TLC chromatogram for each and d) estimating the intensity of any secondary spot obtained from the sample solution which corresponds in Rf value to the compound (1), against the intensity of the spot due to the compound (1) in the chromatogram of the reference solution. It should be noted that the reference solution can be a "mixed" reference solution in that it can contain both the compound (1) and another reference material of known purity, i.e., further containing a known amount and purity of paroxetine and/or other compounds prescribed to be tested, etc.

Similarly an assay using HPLC can also be formulated. The reference standard analytical results may include the resolution factor, response factor, the retention time, and/or the peak area for the compound(1) For example, a process for testing the purity and/or stability to degradation of a sample comprising paroxetine comprises the steps of:

a) dissolving a sample comprising paroxetine in a solvent to produce one or more sample solutions b) dissolving a sample of compound(1) in a solvent to produce a reference solution c) injecting the sample and reference solutions to an HPLC column and d) estimating the peak areas of each solution and calculating from these the content of the in each sample solution.

In this embodiment, it may be necessary or desirable to run a system suitability solution through the HPLC column prior to step c) in order to determine the resolution factor between paroxetine and any other compound present in the sample. In that case the method includes the additional step of b') dissolving paroxetine and a suitable external standard (s) to produce a system suitability solution, and injecting the system suitability solution onto the HPLC column to determine resolution factor(s). This is useful to check that the column is still performing within specifications. The suitability solution can be the solution of compound (1), but it is not limited thereto and can be any material that shows whether the column still works as designed.

As an alternative to assaying a sample of the reference marker separately each time, a parameter known as the Response factor (R) may be used. The response factor is a previously determined ratio of a numerical result (e.g. peak area at HPLC) obtained by testing a sample of the compound (1), by a given analytical technique, to the corresponding numerical result obtained by testing the same amount of pure paroxetine at an equivalent concentration. The known response factor for compound (1) can be used to calculate the amount of that particular marker in the test sample. In this way, the relative amount of the impurity to the impurity in the sample can be determined as is well known in the art.

In the above embodiments, the need for the solvent to dissolve the paroxetine sample should be understood to require only dissolution of the paroxetine substance and the impurities of interest. Other components such as inert fillers in a pharmaceutical composition need not be soluble in the solvent system and need not be "dissolved" in order to meet the above "dissolving" step, as is conventional in the art for assaying a pharmaceutical dosage form.

Typically pharmaceutical compositions are made in batches or lots for production purposes. Production lots are typically 100,000 to 1,000,000 or more tablets or capsules. A production lot should be checked to insure that the level of compound (1) is within specification; i.e., a quality control test. A sample from the production lot (e.g. 10 to 100 capsules or tablets) is taken and assayed for the presence of N-formyl paroxetine of formula (1) and preferably also for the content of the same. If a sample passes the assay then the production lot can be sold or released to the public including its use in clinical studies. A sample "passes" the assay when the amount of N-formyl paroxetine does not exceed a predetermined upper limit. In some cases, the predetermined upper limit is the detection limit of the assay: if the assay can detect any N-formyl paroxetine then the sample does not pass and the production lot is not sold or released. Suitable upper limits include 0.01%, 0.05%, 0.1%, 0.2% and 0.3% of N-formyl paroxetine based on the weight of the paroxetine compound. Preferred paroxetine pharmaceutical compositions contain paroxetine, paroxetine hydrochloride, paroxetine maleate, paroxetine acetate, or paroxetine methane sulfonate as the active ingredient.

The same strategy can be applied for production lots of paroxetine substance. A sample from the production lot (e.g. 0.5 g of the material) is taken and assayed for the presence of compound (1) and preferably also for the content of the same. Typically the paroxetine substance should contain less than 0.2%, more preferably less than 0.1% compound (1) based on the amount of paroxetine (in terms of a free base). Generally the entire production lot, minus any retained sample(s), will be sold or otherwise released by the manufacturer unless an unacceptable level of compound (1) is found. In that case, the production lot will not be sold or released; i.e. neither placed in commerce nor used in production of pharmaceutical products.

The following examples illustrate the invention but it should be understood that the present invention is by no means restricted to these specific examples.

EXAMPLE 1

Reaction Scheme:

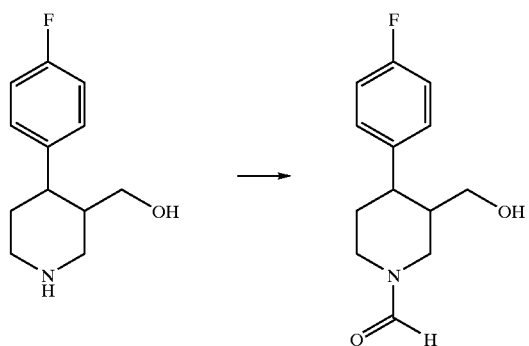

4.3 g of a compound of formula (4) was added to 25 ml methyl formate, a turbid suspension was obtained which was stirred at room temperature for 1 hour. The methyl formate was evaporated under reduced pressure. A slightly yellow oil was obtained. Yield: 4.4 g (100%) of N-formyl paroxol, a compound of formula (2).

EXAMPLE 2a

Reaction Scheme :

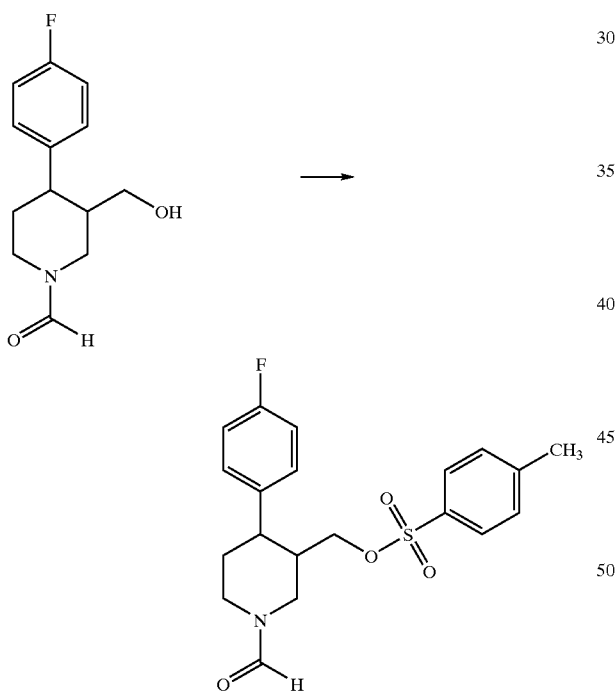

4.0 g n-formyl-paroxol was dissolved in 40 ml toluene. 2.05 g triethylamine was added. The stirred solution was cooled to 5–12° C. and 3.86 g tosyl chloride was added portionwise in 15 minutes. The resulting mixture was allowed to warm up to room temperature and stirred for 18 hours. 2.05 g triethylamine was added, 3.86 g tosyl chloride was added (at room temperature). Stirring was continued for 24 hours. 40 ml of the reaction mixture was filtered and the filtrate was evaporated under reduced pressure. The residue was purified over Silica 60 using ethyl acetate as mobile phase. Yield: 1.5 g of tosyl-formyl-paroxol.

EXAMPLE 2b 1.0 g Tosyl-formyl-paroxol was dissolved in 5 ml dry THF. 100 mg NaH 60% disp. in oil was added to a solution of 350 mg sesamol in 5 ml dry THF. Hydrogen gas was formed and to this solution the tosyl-formyl solution was added and stirred for 1 hour at room temperature. 1.8% conversion was observed (HPLC). The reaction mixture was heated to 60° C. for 1 night. 50 mg NaH 60% disp. in oil was added and stirred for 40 minutes. 100 mg NaH 60% disp. in oil and 350 mg sesamol was added and stirred for 1 night at 60° C. 50 mg NaH 60% disp. in oil and 175 mg sesamol was added and stirred for 4 hours at room temperature. The reaction mixture was cooled to room temperature and 20 ml ethyl acetate was added. The resulting solution was washed with 2×10 ml 5% $NaHCO_3$ solution and 2×10 ml 1 N NaOH solution. The organic layer was dried on $Na_2SO_4$ and evaporated to dryness under reduced pressure. Yield: 0.9 g of an N-formyl paroxetine compound of formula (1) crude product.

EXAMPLE 3

Reaction Scheme :

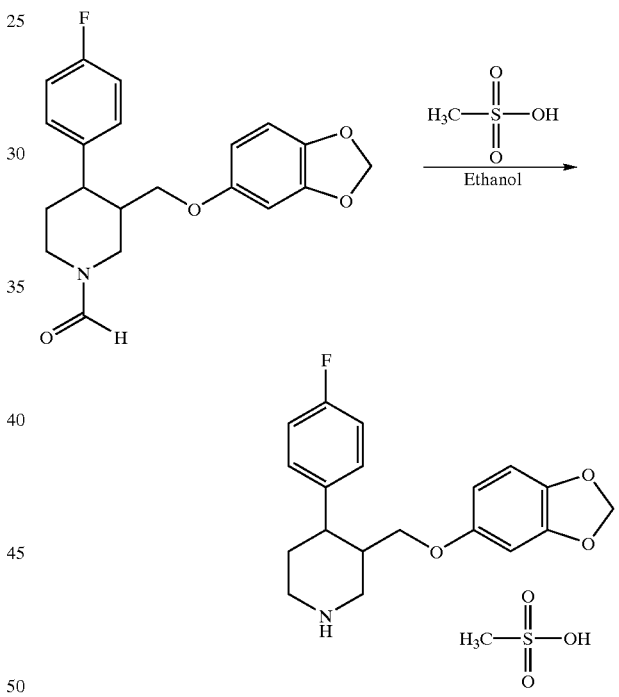

200 mg of N-formyl paroxetine compound of formula (1) was dissolved in 2 ml ethanol. 100 mg of methane sulfonic acid was added thereto. The resulting solution was refluxed for 7 hours. The solution was allowed to cool to room temperature. A crystal of paroxetine methane sulfonate was added to induce crystallization. The resulting suspension was stirred for 16 hours at room temperature. The solid was filtered off and dried under vacuum at 40° C. for 1 hour. Yield: 110 mg (46%) of paroxetine methane sulfonate having a purity (HPLC) of 99.5%.

EXAMPLE 4

0.51 g of paroxetine free base was added to 5 ml of formic acid and the mixture was heated to 60° C. 3 ml of acetic acid anhydride was added dropwise to the solution. After approximately 15 minutes at 60° C., the mixture was cooled and evaporated. Yield approx. 95% of N-formyl paroxetine compound of formula (1) as an oily product.

EXAMPLE 5

13.6 g (41.3 mmol) of paroxetine free base was dissolved in 80 ml formic acid (exotherm reaction). 40 ml acetic acid anhydride was dropwise added. After complete addition, the mixture was heated on an 65° C. oil bath for 0.5 hours. The mixture was evaporated yielding an oil, which was dissolved in 60 ml of ethyl acetate and washed with 3×20 ml of saturated NaHCO$_3$ solution and once with water (20 ml). The organic layer was dried over Na$_2$SO$_4$ and evaporated yielding 14.12 g of the product (~95.7%). NMR and IR spectra confirmed the structure to be an N-formyl paroxetine compound of formula (1) with a purity (HPLC analysis) of 98%.

The invention having been thus described it will be apparent to the worker of ordinary skill in the art that the same may be modified in many ways without departing from the spirit or scope of the invention and all such modifications are included within the scope of the following claims.

We claim:

1. A substantially pure and isolated N-formyl paroxetine of formula (1)

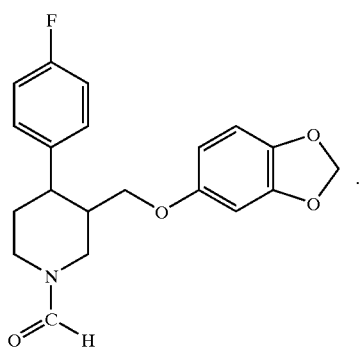

(1)

2. The compound according to claim 1, wherein said compound is in the form of an oil.

3. The compound according to claim 1, wherein said compound contains not greater than 10% impurities.

4. The compound according to claim 1, wherein said N-formyl paroxetine is the trans-3S, 4R enantiomer.

5. A composition which comprises an N-formyl paroxetine of formule (1).

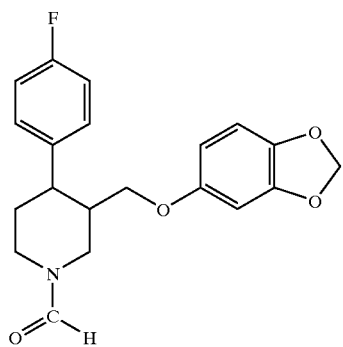

(1)

and 0.1% to 99.97% of a paroxetine compound, based on the combined weight of said N-formyl paroxetine and said paroxetine compound.

6. The composition according to claim 5, which comprises 1% to 99.89% of said paroxetine compound.

7. The composition according to claim 6, which comprises 1% to 99.8% of said paroxetine compound.

8. The composition according to claim 7, which comprises 10% to 99.7% of said paroxetine compound.

9. The composition according to claim 5, wherein said paroxetine compound is selected from the group consisting of paroxetine, paroxetine hydrochloride, paroxetine maleate, paroxetine acetate, and paroxetine mesylate.

10. The composition according to claim 5, which further comprises a pharmaceutically acceptable excipient.

11. The composition according to claim 10, wherein said at least one excipient comprises a calcium phosphate.

12. A pharmaceutical composition for treating a selective serotonin reuptake inhibitor-treatable disease or condition, comprising an effective amount of a paroxetine agent and at least one pharmaceutically acceptable excipient, wherein said paroxetine agent consists of an N-formyl paroxetine compound of formula (1) and 0 to 99,97 % of a paroxetine compound, based on the combined weight of said N-formyl paroxetine and said paroxetine compound:

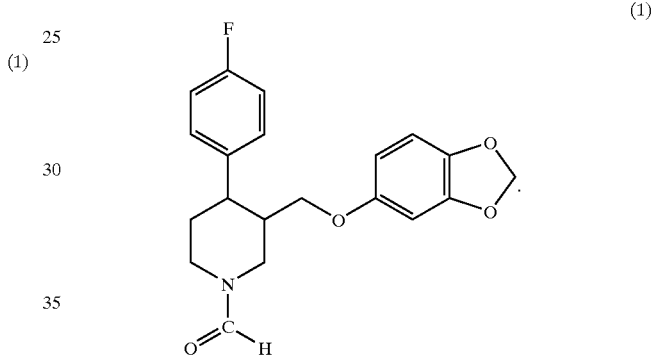

(1)

13. A composition comprising a N-formyl Paroxetine of formula (1),

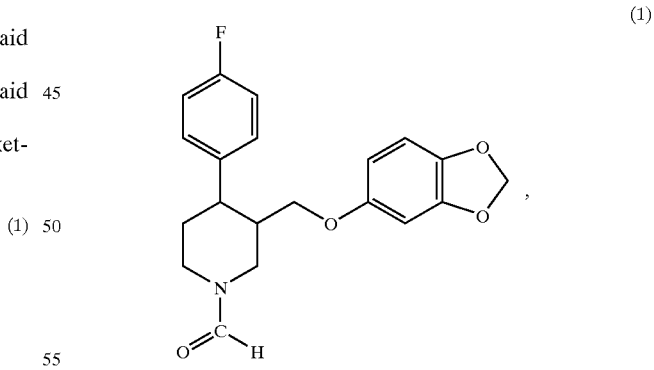

(1)

0 to 99.97% of a paroxetine compound, based on the combined weight of said N-formyl paroxetine and said paroxetine compound, and at least one ingredient selected from the group consisting of binders, fillers, carriers, preservatives, and combinations thereof.

14. The composition according to claim 13, wherein said composition contains 0 to 5% of paroxetine compound.

15. The composition according to claim 13, wherein said composition is in a liquid form.

* * * * *